US009877724B2

(12) United States Patent
Gagner et al.

(10) Patent No.: US 9,877,724 B2
(45) Date of Patent: Jan. 30, 2018

(54) METHODS AND DEVICES FOR ENDOSCOPICALLY CREATING AN ANASTOMOSIS

(75) Inventors: Michel Gagner, Montréal (CA); David J. Blaeser, Brooklyn Park, MN (US); Dale A. Spencer, Wayzata, MN (US)

(73) Assignee: Michel Gagner, Montréal, QC (CA)

( * ) Notice: Subject to any disclaimer, the term of this patent is extended or adjusted under 35 U.S.C. 154(b) by 660 days.

(21) Appl. No.: 12/809,709

(22) PCT Filed: Dec. 19, 2008

(86) PCT No.: PCT/US2008/087792
§ 371 (c)(1),
(2), (4) Date: Sep. 22, 2010

(87) PCT Pub. No.: WO2009/082710
PCT Pub. Date: Jul. 2, 2009

(65) Prior Publication Data
US 2011/0009886 A1    Jan. 13, 2011

Related U.S. Application Data

(60) Provisional application No. 61/016,221, filed on Dec. 21, 2007.

(51) Int. Cl.
*A61B 17/11*      (2006.01)
*A61B 17/3205*    (2006.01)
*A61B 17/00*      (2006.01)

(52) U.S. Cl.
CPC ..... *A61B 17/1114* (2013.01); *A61B 17/32053* (2013.01); *A61B 2017/00469* (2013.01); *A61B 2017/00876* (2013.01); *A61B 2017/1103* (2013.01); *A61B 2017/1117* (2013.01); *A61B 2017/1139* (2013.01)

(58) Field of Classification Search
CPC ................. A61B 17/1114; A61B 17/11; A61B 2017/1107; A61B 2017/111; A61B 2017/1117; A61B 2017/1139; A61B 2017/1103
USPC ........ 606/153, 157, 213, 139–141, 215, 216
See application file for complete search history.

(56) References Cited

U.S. PATENT DOCUMENTS

| | | |
|---|---|---|
| 3,358,676 A | 12/1967 | Heinrich et al. |
| 4,548,201 A | 10/1985 | Yoon |
| 4,567,891 A | 2/1986 | Kanshin et al. |
| 4,917,087 A | 4/1990 | Walsh et al. |
| 4,964,863 A | 10/1990 | Kanshin et al. |
| 5,250,058 A | 10/1993 | Miller et al. |
| 5,595,562 A | 1/1997 | Grier |
| 5,690,656 A | 11/1997 | Cope et al. |
| 5,895,404 A | 4/1999 | Ruiz |

(Continued)

FOREIGN PATENT DOCUMENTS

| | | |
|---|---|---|
| EP | 1616526 A1 | 1/2006 |
| WO | 2007080110 A1 | 7/2007 |

(Continued)

*Primary Examiner* — Jocelin Tanner
(74) *Attorney, Agent, or Firm* — Inskeep IP Group, Inc.

(57) ABSTRACT

A method and devices that endoscopically create an anastomosis between two sections of the digestive tract, thereby allowing at least some chyme to bypass a section of the digestive tract while, optionally, the remaining chyme passes through the entire tract.

10 Claims, 17 Drawing Sheets

(56) References Cited

U.S. PATENT DOCUMENTS

| | | |
|---|---|---|
| 6,352,543 B1 | 3/2002 | Cole |
| 6,524,322 B1 | 2/2003 | Berreklouw |
| 6,547,798 B1 * | 4/2003 | Yoon et al. ............... 606/141 |
| 6,632,229 B1 | 10/2003 | Yamanouchi |
| 6,682,540 B1 | 1/2004 | Sancoff et al. |
| 6,884,250 B2 * | 4/2005 | Monassevitch et al. ..... 606/153 |
| 7,211,094 B2 | 5/2007 | Gannoe et al. |
| 7,211,095 B2 | 5/2007 | Bachinski et al. |
| 7,282,057 B2 | 10/2007 | Surti et al. |
| 7,654,951 B2 | 2/2010 | Ishikawa |
| 7,938,841 B2 | 5/2011 | Sharkawy et al. |
| 2002/0049459 A1 | 4/2002 | Kato |
| 2002/0072758 A1 | 6/2002 | Reo et al. |
| 2003/0225312 A1 | 12/2003 | Suzuki et al. |
| 2004/0015179 A1 * | 1/2004 | Monassevitch et al. ..... 606/153 |
| 2004/0225191 A1 | 11/2004 | Sekine et al. |
| 2005/0277964 A1 | 12/2005 | Brenneman et al. |
| 2006/0011698 A1 * | 1/2006 | Okada et al. ............ 227/175.1 |
| 2006/0085035 A1 * | 4/2006 | Viola ....................... 606/219 |
| 2006/0085060 A1 | 4/2006 | Campbell |
| 2006/0142790 A1 | 6/2006 | Gertner |
| 2007/0135802 A1 | 6/2007 | Suzuki et al. |
| 2007/0260214 A1 | 11/2007 | Mikkaichi et al. |
| 2007/0276378 A1 * | 11/2007 | Harrison ............ A61B 17/0483 606/309 |
| 2008/0114384 A1 | 5/2008 | Chang et al. |
| 2008/0200934 A1 * | 8/2008 | Fox ............................ 606/153 |
| 2008/0208224 A1 | 8/2008 | Surti et al. |
| 2008/0208244 A1 | 8/2008 | Boylan et al. |
| 2009/0125042 A1 | 5/2009 | Mouw |
| 2009/0227828 A1 | 9/2009 | Swain et al. |
| 2010/0036399 A1 | 2/2010 | Viola |
| 2010/0256659 A1 | 10/2010 | Aguirre et al. |
| 2011/0009886 A1 | 1/2011 | Gagner et al. |
| 2011/0144560 A1 | 6/2011 | Gagner et al. |
| 2012/0259350 A1 | 10/2012 | Gagner et al. |
| 2013/0138126 A1 | 5/2013 | Gagner et al. |
| 2013/0150873 A1 | 6/2013 | Gagner et al. |

FOREIGN PATENT DOCUMENTS

| | | |
|---|---|---|
| WO | 2009082710 A1 | 7/2009 |
| WO | 2011008988 A1 | 1/2011 |

* cited by examiner

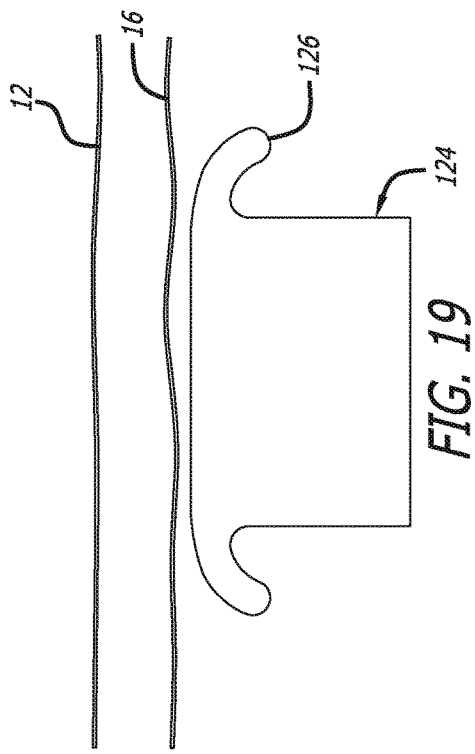
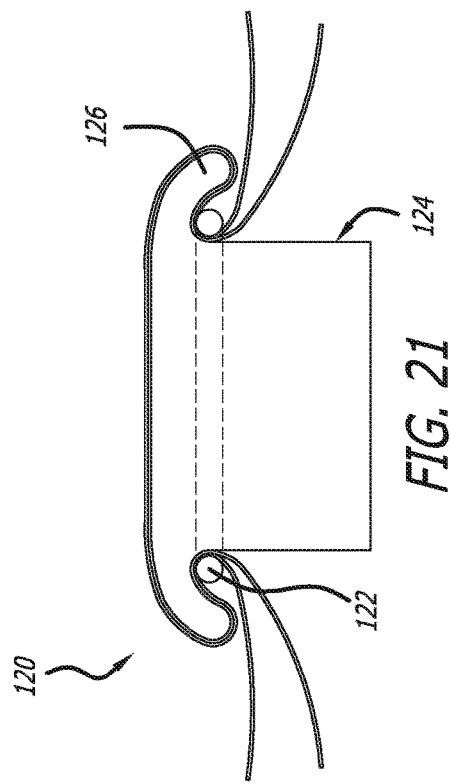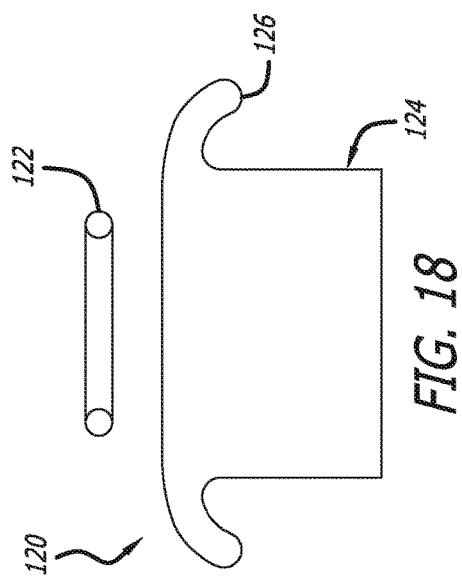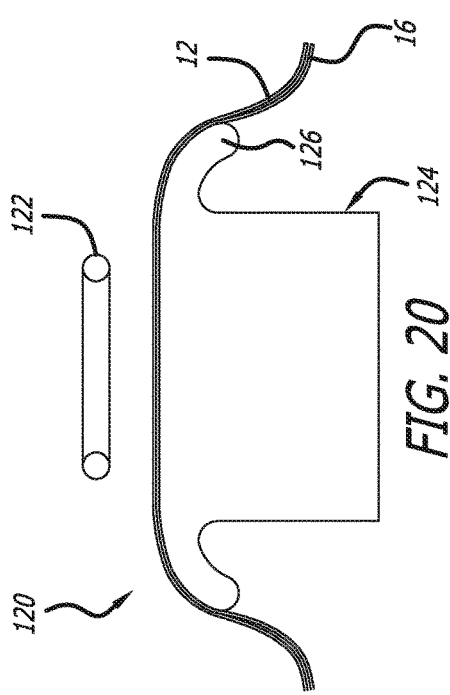

METHODS AND DEVICES FOR ENDOSCOPICALLY CREATING AN ANASTOMOSIS

RELATED APPLICATIONS

This application claims priority from related U.S. provisional application Ser. No. 61/016,221 filed Dec. 21, 2007, entitled Methods and Devices for Endoscopically Creating an Anastomosis, the entirety of which is hereby incorporated by reference.

BACKGROUND OF THE INVENTION

The present invention relates generally to addressing problems related to the digestive system, particularly obesity and type II diabetes. Additionally, it is contemplated that the methods and devices of the present invention may be used in treating other digestive conditions such as benign or malignant obstructions of the stomach, small bowel and/or colon when clinically indicated; peptic ulcer disease; inflammatory bowel disease; adhesions; annular pancreas; duodenal, pancreatic, intestinal, or colonic primary malignancies; and secondary malignancies.

Obesity

According to the Center for Disease Control (CDC), sixty six percent of the United States population are overweight, and thirty two percent are obese, presenting an overwhelming health problem. From an economic standpoint, it is estimated that more than 100 billion dollars are spent on obesity and treating its major co-morbidities. This figure does not include psychological and social costs. Many health care experts consider obesity the largest health problem facing westernized societies and considered obesity an epidemic. From a medical standpoint, obesity is the primary risk factor for type 2 diabetes and obstructive sleep apnea. It increases the chances for heart disease, pulmonary disease, infertility, osteoarthritis, cholecystitis and several major cancers, including breast and colon cancers. Despite these alarming facts, treatment options for obesity remain limited.

Treatment options include dietary modification, very low-calorie liquid diets, pharmaceutical agents, counseling, exercise programs and surgery. Diet and exercise plans often fail because most individuals do not have the discipline to adhere to such plans. When diet and exercise fail, many try dietary supplements and drugs or other ingestible preparations promoted as being capable of suppressing appetite or inducing satiety. In general, these techniques for treating compulsive overeating/obesity have tended to produce only a temporary effect. The individual usually becomes discouraged and/or depressed after the initial rate of weight loss plateaus and further weight loss becomes harder to achieve. The individual then typically reverts to the previous behavior of compulsive overeating.

Surgical procedures that restrict the size of the stomach and/or bypass parts of the intestine are the only remedies that provide lasting weight loss for the majority of morbidly obese individuals. Surgical procedures for morbid obesity are becoming more common based on long-term successful weight loss result.

Bariatric surgery is a treatment for morbid obesity that involves alteration of a patient's digestive tract to encourage weight loss and to help maintain normal weight. Known bariatric surgery procedures include jejuno-ileal bypass, jejuno-colic shunt, biliopancreatic diversion, gastric bypass, Roux-en-Y gastric bypass, gastroplasty, gastric banding, vertical banded gastroplasty, and silastic ring gastroplasty. A more complete history of bariatric surgery can be found on the website of the American Society for Bariatric Surgery at http://www.asbs.org, the contents of which are incorporated by reference herein in their entirety.

The surgeries which create malabsorption, such as the by-pass operations, although effective in weight reduction, involve permanent modification of the GI tract and have a risk of short and long term complication and even death.

Gastric bypass is the most common weight loss operation in the United States. This procedure reduces the size of the stomach and shortens the effective-length of intestine available for nutrient absorption. With gastric bypass many investigators have reported weight loss results that exceed 70% of excess weight. However, this efficacy does not come without complication. The accepted mortality of the procedure is 1 in 200. Additionally, because various sections of the intestine are responsible for absorbing various nutrients from the chyme being digested, bypassing sections of the intestine can result in an inability of the modified digestive tract to benefit from certain nutrients. In certain cases, this results in conditions such as anemia and must be treated with high doses of vitamin or nutrient supplements.

Diabetes

According to the National Institute of Diabetes and Digestive and Kidney Diseases (NIDDK) an estimated 20.8 million people in the United States, 7.0 percent of the population, have diabetes, a serious, lifelong condition. Of those, 14.6 million have been diagnosed, and 6.2 million have not yet been diagnosed. In 2005, about 1.5 million people aged 20 or older were diagnosed with diabetes. According to the American Diabetes Association, the total annual economic cost of diabetes in 2002 was estimated to be $132 billion.

Diabetes is a set of related diseases in which the body cannot regulate the amount of sugar (glucose) in the blood. Glucose in the blood provides the body with energy. In a healthy person, the blood glucose level is regulated by several hormones including insulin, glucagons, and epinephrine. Insulin is produced by the pancreas, a small organ near the stomach that also secretes important enzymes that help in the digestion of food. Insulin allows glucose to move from the blood into the liver, muscle, and fat cells, where it is used for fuel.

At least 90% of patients with diabetes have Type 2 diabetes wherein the pancreas secretes insulin but the body is partially or completely unable to use the insulin. This is sometimes referred to as insulin resistance. The body tries to overcome this resistance by secreting more and more insulin. People with insulin resistance develop Type 2 diabetes when they do not continue to secrete enough insulin to cope with the higher demands.

Recently, evidence for reduction of complications of type 2 diabetes with tight control of hyperglycemia has been reported, but current therapies, including diet, exercise, behavior modification, oral hypoglycemic agents, and insulin, rarely return patients to euglycemia.

For reasons not completely known, the majority of patients who undergo gastric bypass surgery experience resolution of Type 2 diabetes and enjoy normal blood glucose and glycosylated hemoglobin levels with discontinuation of all diabetes-related medications. One hypothesis, that has been proposed, is that diabetes control results from the expedited delivery of nutrient-rich chyme (partially digested food) to the distal intestines, enhancing a physiologic signal that improves glucose metabolism, the so called "hindgut hypothesis". However, because gastric bypass surgery is considered a relatively high-risk major surgery, it is not used to treat Type 2 diabetes.

OBJECTS AND SUMMARY OF THE INVENTION

The methods and devices of the present invention are directed to a minimally invasive, endoscopic solution for treating patients with obesity and/or Type 2 diabetes. The solution is simple, user-friendly, reversible, and does not require a permanent implant. The procedure is performed endoscopically, thus obviating the need for abdominal incisions. This procedure has the potential of being performed outside of the operating room, potentially in an endoscopy suite.

One aspect of the present invention treats the aforementioned conditions by creating a partial bypass of a portion of the small intestines. Preferably, a small anastomosis is created between the third section of the duodenum and the ileum.

This solution creates an alternative pathway for chyme. A portion of the nutrients will bypass a portion of the small intestines and thus not be absorbed (controlled absorption). The amount of bypass is controlled by the size of the anastomosis. The physician is thus able to vary the size of the anastomosis both at the time of the procedure and during subsequent follow-up procedures. The anastomosis also provides a bypass for nutrient-rich chyme to enter the ileum. This is thought to have the effect of triggering early satiety as well as improving glucose metabolism. A potential candidate mediator of this effect is glucagon-like peptide 1 (GLP-1). This incretin hormone is secreted by cells in the distal bowel in response to nutrients, which stimulates insulin secretion.

Another aspect of the present invention provides a method by which an endoscope is advanced from the stomach into the duodenum. Another endoscope is advanced from the large intestines into the ileum. The normal anatomy in a human is such that the third section of the duodenum is in close proximity to the ileum and thus if either structure is illuminated from within it can readily be seen from the other. For example, if the duodenum is illuminated, the light can be seen with an endoscope in the ileum and the ileum can then be gently maneuvered such that it is touching the duodenum.

Once intimate contact has been confirmed from within the duodenum and the ileum, a hollow needle is passed between the structures. A wire is passed through the needle and advanced outside of the body. One component of the anastomosis device is then advanced along the wire approaching the anastomosis site from either side. The two halves are then joined and create intimate contact between the serosal surfaces of the two vessels. The configuration of the contact point can be generally circular or elliptical. During the healing period the tissue is compressed and becomes necrotic. The tissue around the outside of the anastomosis device is compressed at a lower force. This tissue forms a ring of healed tissue. After a few weeks the necrotic tissue, along with the device detach and are expelled. There is no flow between vessels during the healing period. Everything flows through the natural distal duodenum and thus there is no risk of obstructing flow. Human serosal tissue that is placed in intimate contact has been shown to heal within 7 days.

Patients can be tracked and if absorption needs to be further limited a follow up procedure can be performed to create additional anastomosis in the same or other locations or make the anastomosis larger.

BRIEF DESCRIPTION OF THE DRAWINGS

FIGS. 18-21 depict a deployment sequence of an embodiment of an anastomosis device of the present invention;

DETAILED DESCRIPTION OF THE INVENTION

Figure 42:
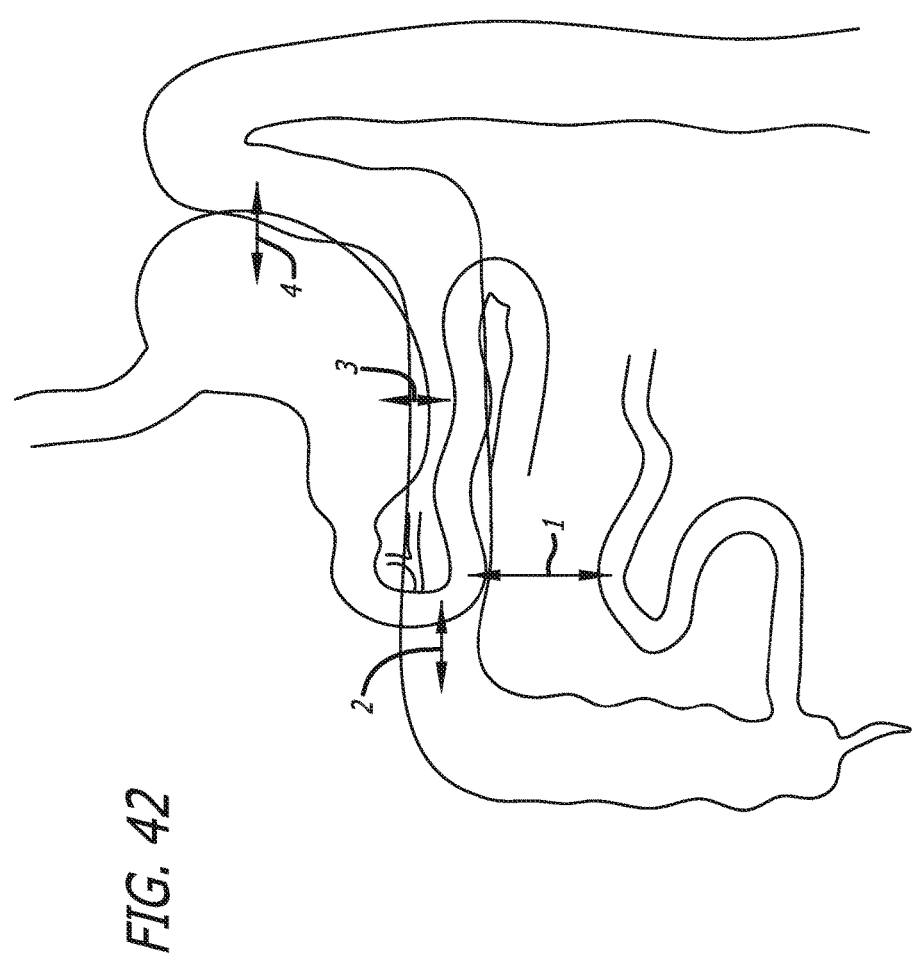

The present invention includes a method of endoscopically creating an anastomosis as well as several devices that can be used to form the anastomosis. FIGS. 1-7 show a series of diagrams detailing the various steps of the method. The remaining figures depict several embodiments of various devices. By explaining the method first, the various embodiments of devices will be more easily understood. It is important to note that the method is described as forming an anastomosis between the duodenum and the ileum. These locations are provided by way of example only. One skilled in the art will realize that the sections of the digestive tract joined using the method of the present invention is a determination that is patient-dependent and is to be decided by a physician. For example, if a patient is extremely obese, it may be desired to an anastomosis between the stomach and the colon. FIG. 42 shows several examples of anastomosis sites. Arrow 1 indicates a duodenal-ileal anastomosis. Arrow 2 illustrates a duodenal-colic anastomosis. Arrow 3 indicates a gastro-transverse colic anastomosis. Arrow 4 illustrates a gastro-colic anastomosis. Not shown in this figure, but also envisioned, are jejenal-jejenal anastomosis and duodenal-jejenal anastomosis.

Method

Figure 1:
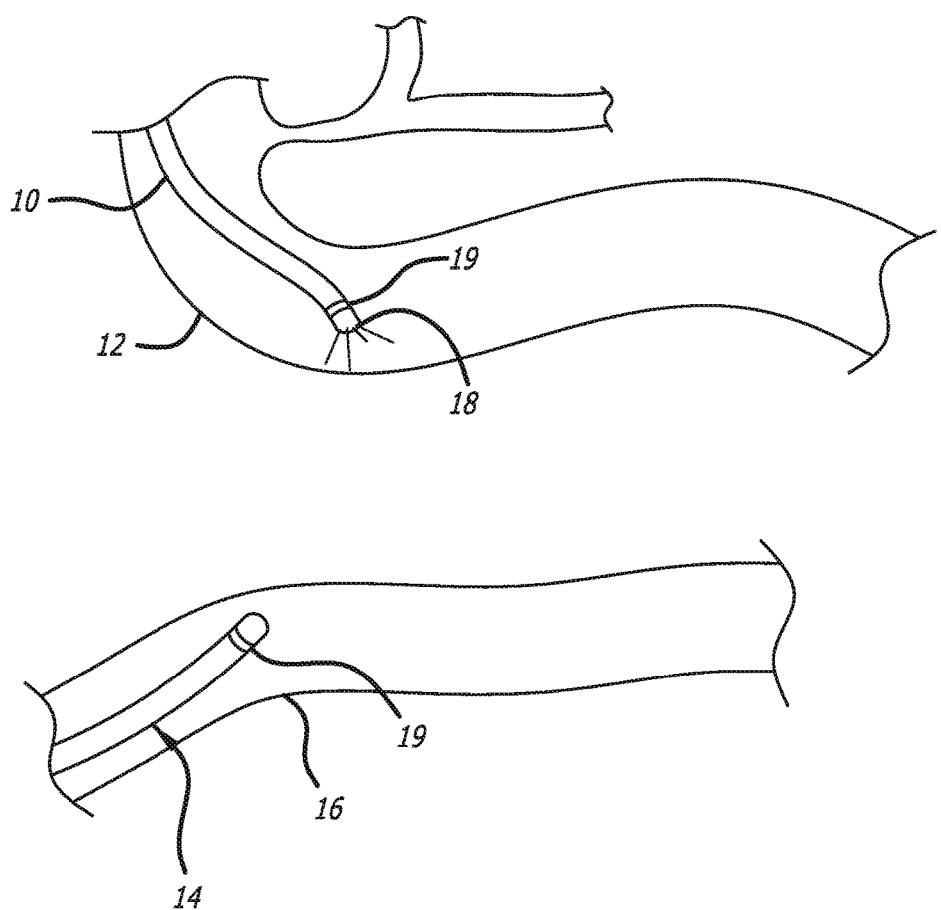
FIGS. 1-7 illustrate steps in a method of the present invention.

Referring first to FIG. 1, the present invention provides a method by which an endoscope 10 is advanced from the stomach into the duodenum 12. A second endoscope 14 is advanced from the large intestines into the ileum 16. The normal anatomy in a human is such that the third section of the duodenum 12 is in close proximity to the ileum 16 and thus if either structure is illuminated from within it can readily be seen from the other. Hence, the duodenum 12, for example, is illuminated with a light 18 at the tip of the first endoscope 10 and the light can be seen with an endoscope 14 in the ileum 16. Alternatively or additionally, each endoscope 10 and 14 may be equipped with a strong magnet 19. The magnets 19 would then be able to automatically align and connect the two endoscopes 10 and 14 when in operational proximity to each other's magnetic fields.

Figure 2:
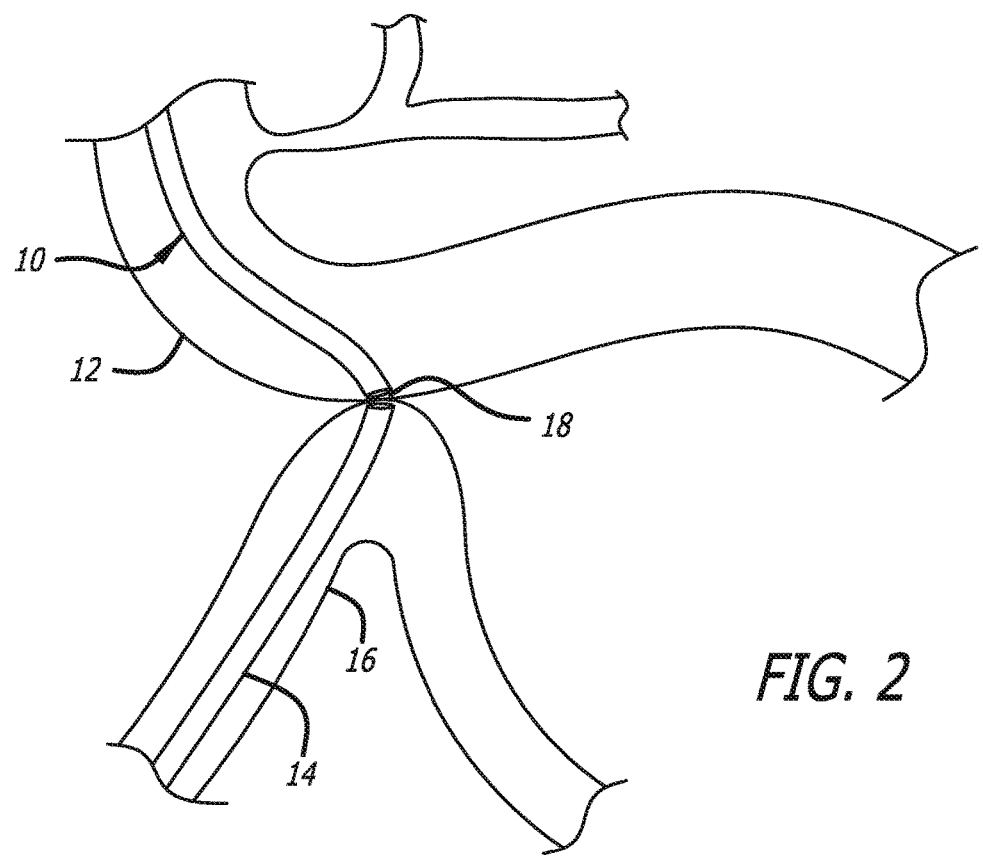

Next, as shown in FIG. 2, the ileum 16 is gently maneuvered such that it is touching the duodenum 12. Though it is preferably to maneuver the ileum 16, one skilled in the art will understand that the duodenum 12 may be maneuvered as well, although to a lesser degree as this organ is not as mobile.

Figure 3:
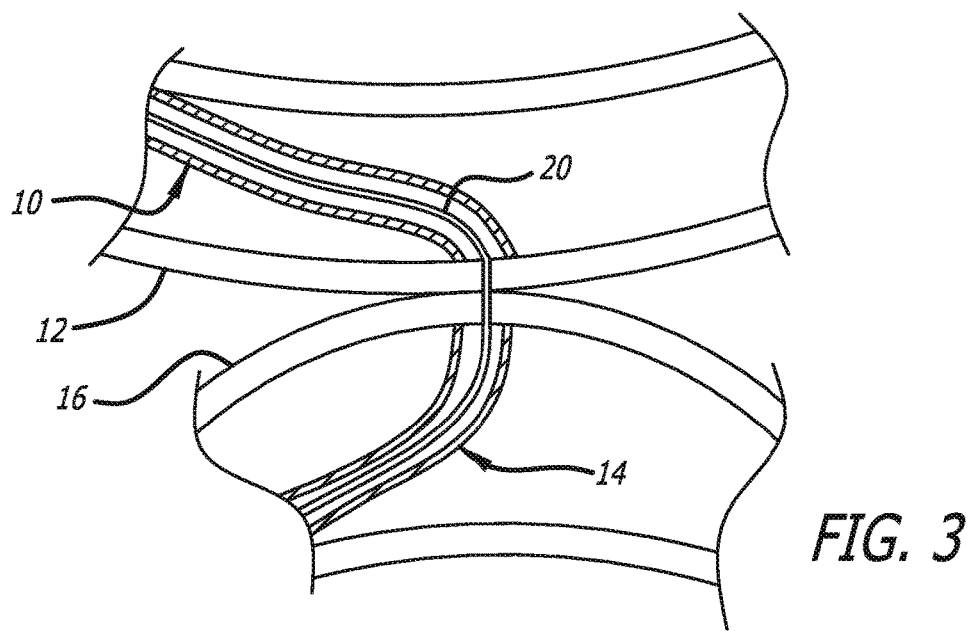

Referring to FIG. 3, once intimate contact has been confirmed from within the duodenum 12 and the ileum 16, a wire 20 is passed through the touching walls of the duodenum 12 and the ileum 16. This may be performed in a variety of ways. For example, the endoscope 10 may have a working channel containing a hollow needle, which may be advanced to pierce the duodenum and ileum, and then the wire 20 may be passed through the needle. Alternatively, the wire 20 may be sharpened and act as a needle. Once passed through to the ileum, the wire 20 may enter a working channel of the second endoscope 14, obviating the need to re-navigate the small and large intestines. Alternatively, a sheath may be advanced over the endoscope 14 and the endoscope retracted as the wire is advanced until the distal end exits the rectum.

Figure 4:
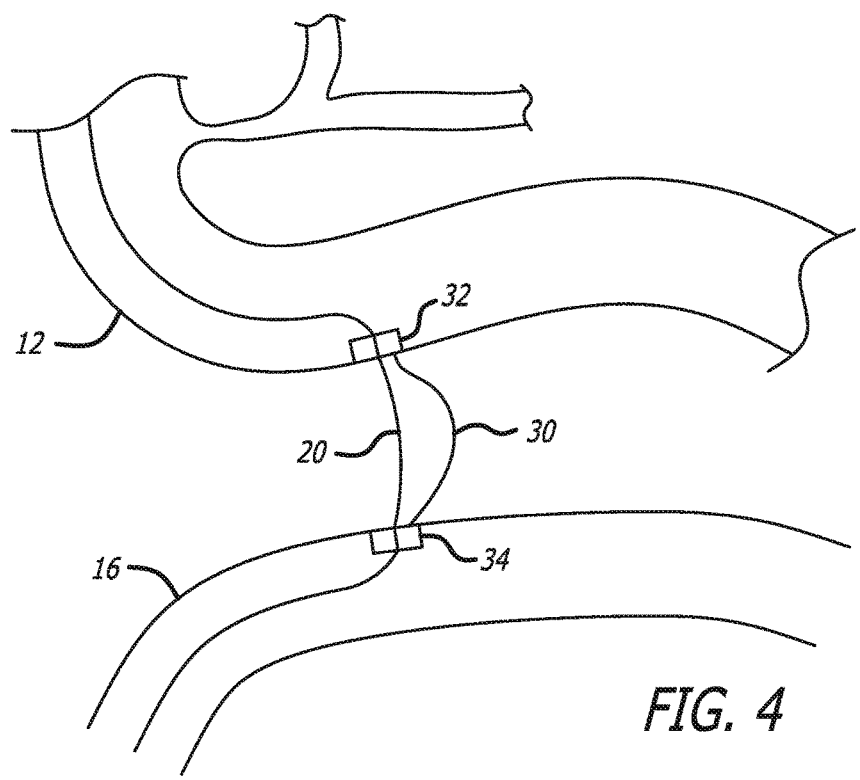

Referring to FIG. 4, next first and second components 32 and 34 of an anastomosis device 30 are advanced over either end of the wire 20. Components 32 and 34 are depicted as generic blocks in these figures as the method is not to be limited to any single device. Rather, several embodiments of anastomosis devices are described below under the heading "Devices."

Figure 5:
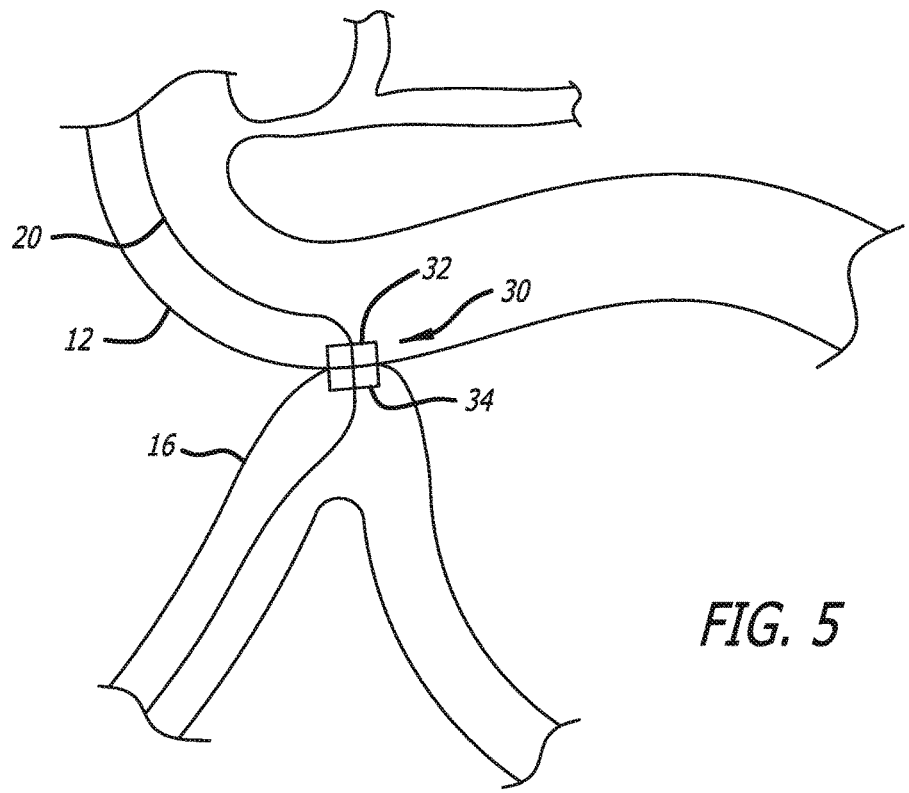

In FIG. 5, the first and second components 32 and 34 of anastomosis device 30 are drawn together and locked. Locking force may be provided by pushing on the first component 32 from the direction of the stomach, while pulling the second component 34. It is also envisioned that if the endoscopes 10 and 14 are equipped with strong magnets 19, the first and second components 32 and 34 may be placed around the end of the endoscopes 10 and 14, distal of the magnets 19. This way, the magnets 19 may be used to provide the force necessary to lock the two components 32 and 34 together. It is also contemplated that this embodiment may completely obviate the need for the wire 20. It is further contemplated that the magnets 19 could serve as the first and second components 32 and 34. In this embodiment, the magnets are held onto the ends of the endoscopes 10 and 14 with an adhesive or magnetic force that is easily overcome by the attractive force between the two magnets 19.

Figure 6:
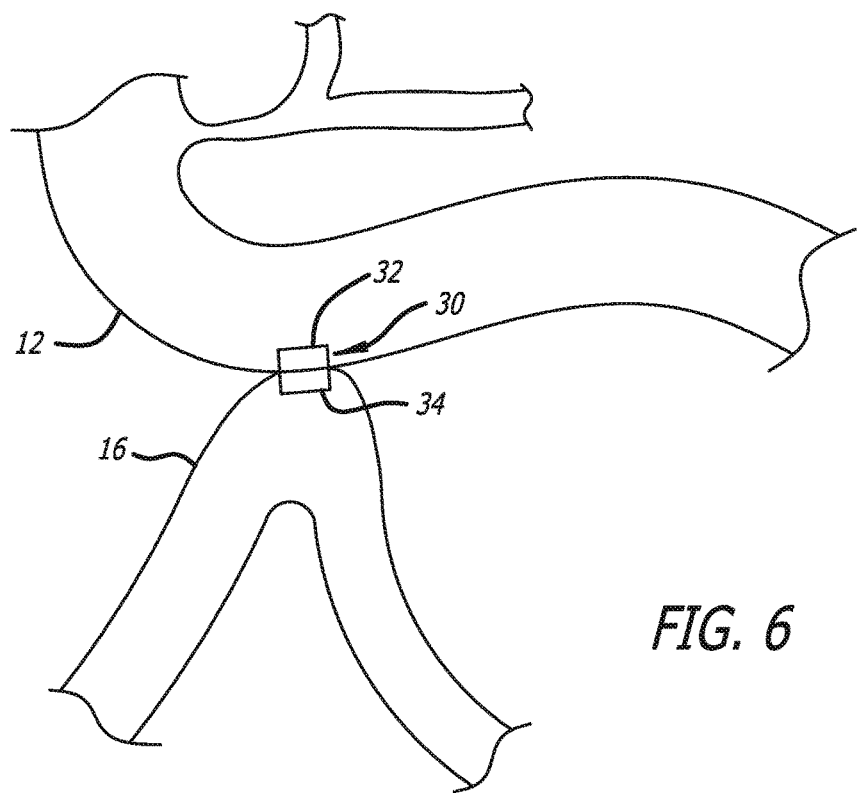
Figure 7:
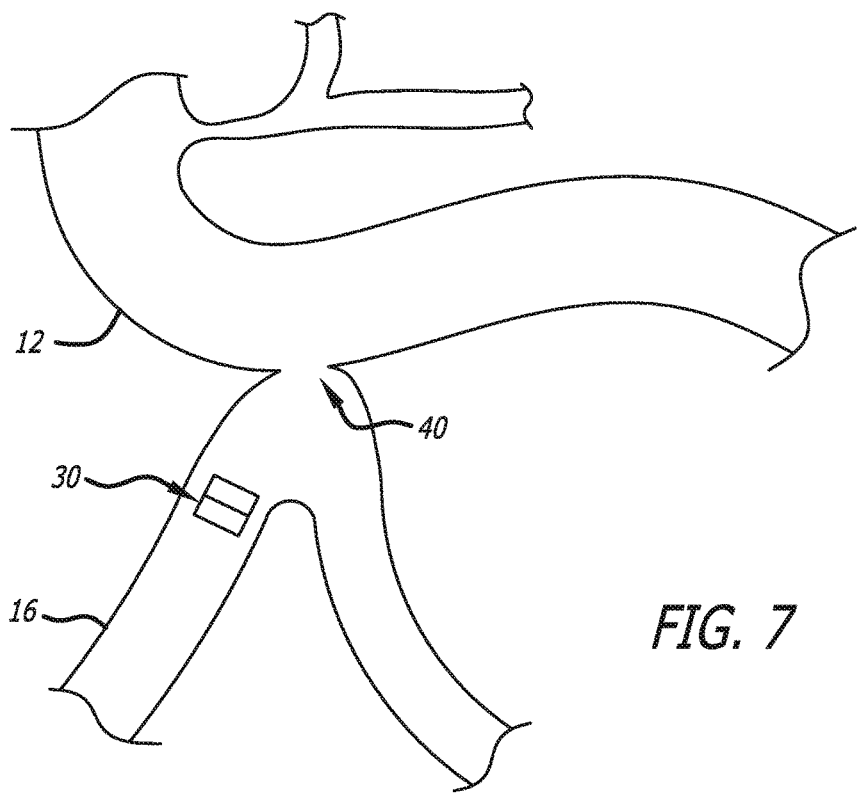

Once the components 32 and 34 are locked, the wire 20 may be removed, as shown in FIG. 6. Locking the first and second components 32 and 34 of the anastomosis device 30 together creates intimate contact between the serosal surfaces of the duodenum 12 and the ileum 16. The configuration of the contacting tissue can be generally circular, elliptical, diamond-shaped, elongate, or shaped like a cross, depending on the configuration of the device 30. During the healing period the tissue is compressed, limiting or eliminating circulation, and the tissue becomes necrotic. The tissue around the outside of the anastomosis device is compressed at a lower force. This tissue forms a ring of healed tissue. Over time, an anastomosis 40 (FIG. 7, for example) is formed and the device 30 is allowed to pass through the digestive system. There is no flow through the anastomosis 40 during the healing period. All chyme flows through the natural distal duodenum and, due to the relatively low profile of the various devices 30, thus there is little risk of obstructing flow. Human serosal tissue that is placed in intimate contact has been shown to heal within 7 days.

Devices

Figure 8:
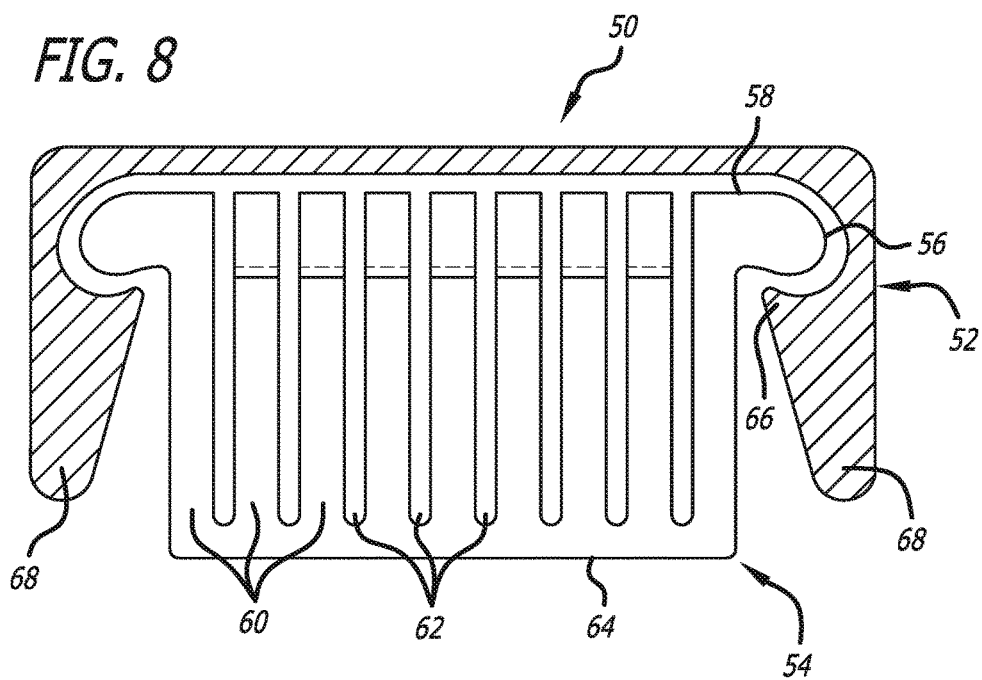
FIG. 8 is a cross-section of an embodiment of an anastomosis device of the present invention.
Figure 9:
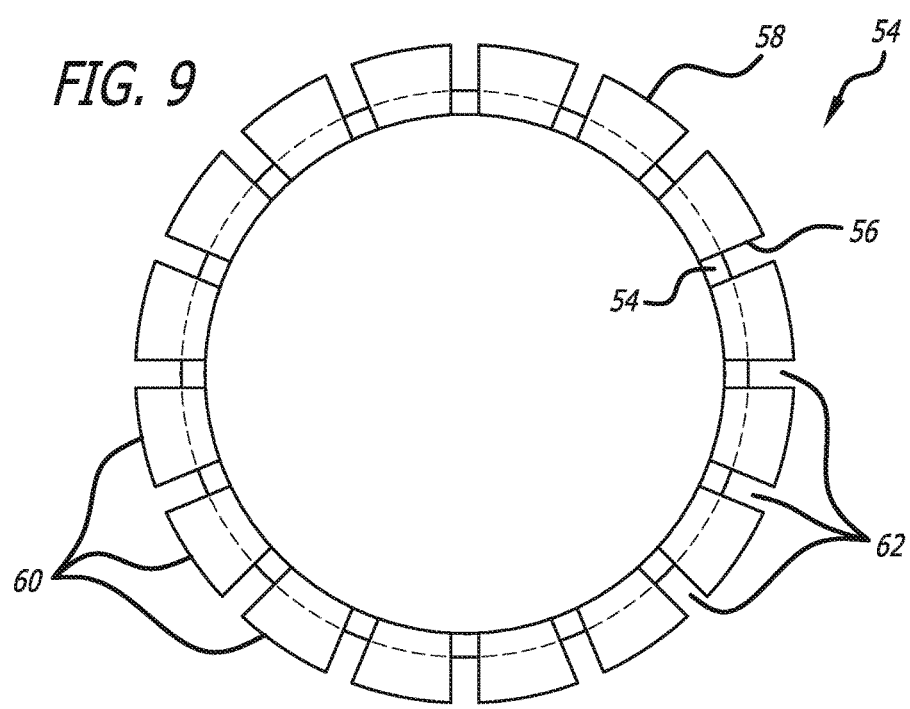
FIG. 9 is a plan view of a component of the device of FIG. 8.

Referring now to FIGS. 8 and 9 there is shown an embodiment of an anastomosis device 50 of the present invention. The device 50 includes a first component 52 and a second component 54 that is configured to mate with the first component 52. The components 52 and 54 are generally circular or oval in shape. The second component 54 is basically a cylindrical wall that forms a lip 56 at a mating end 58. The wall is divided into a plurality of fingers 60 by slots 62 that extend nearly to a non-mating end 64. The slots 62 are necessary to allow the fingers 60 to flex inward when the second component 54 is being connected to the first component 52. The flexibility of the fingers 60 may be varied by varying the length of the slots 62.

The first component 52 is a cylindrical cap that includes an inwardly protruding lip 66 that forms a snap-fit with the lip 56 of the second component 54. Preferably, the first component 52 further includes a tapered extension 58 from the lip 56. The tapered extension 68 places a varying amount of squeezing force on the tissues of the duodenum and ileum such that some tissue necroses while adjacent serosal tissue heals and fuses together.

Figure 10:
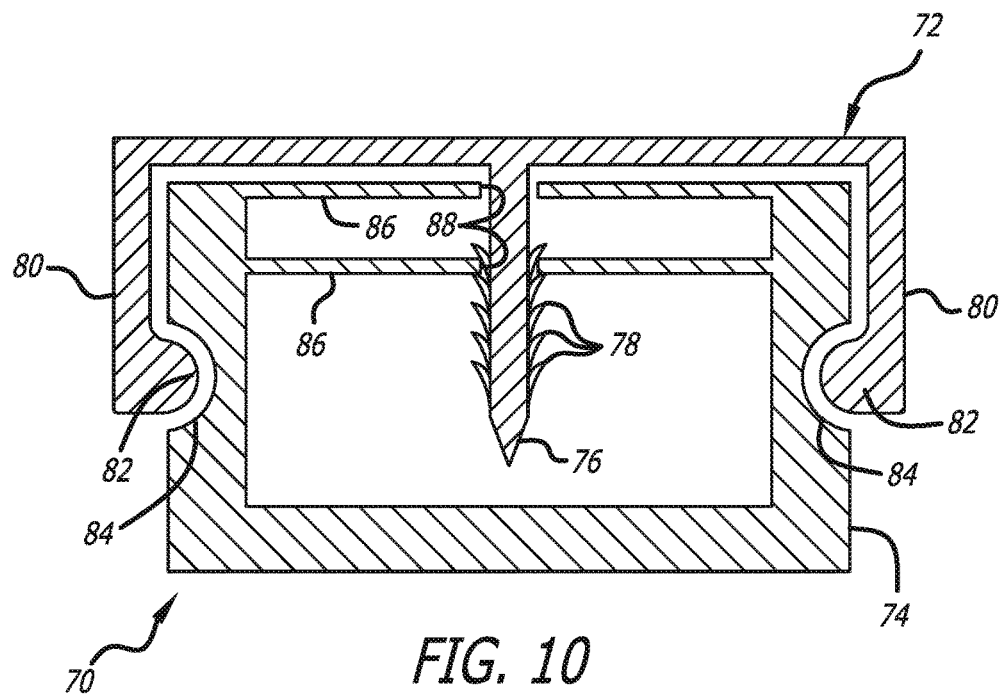
FIG. 10 is a cross-section of an embodiment of an anastomosis device of the present invention.

FIG. 10 shows another embodiment of an anastomosis device 70 of the present invention. The device 70 includes a first component 72 and a second component 74 that is configured to mate with the first component 72. The components 72 and 74 are generally circular or oval in shape. Alternatively, the second component 74 could be one shape, such as circular, while the first component 72 could be another shape such as spoked.

Figure 11:
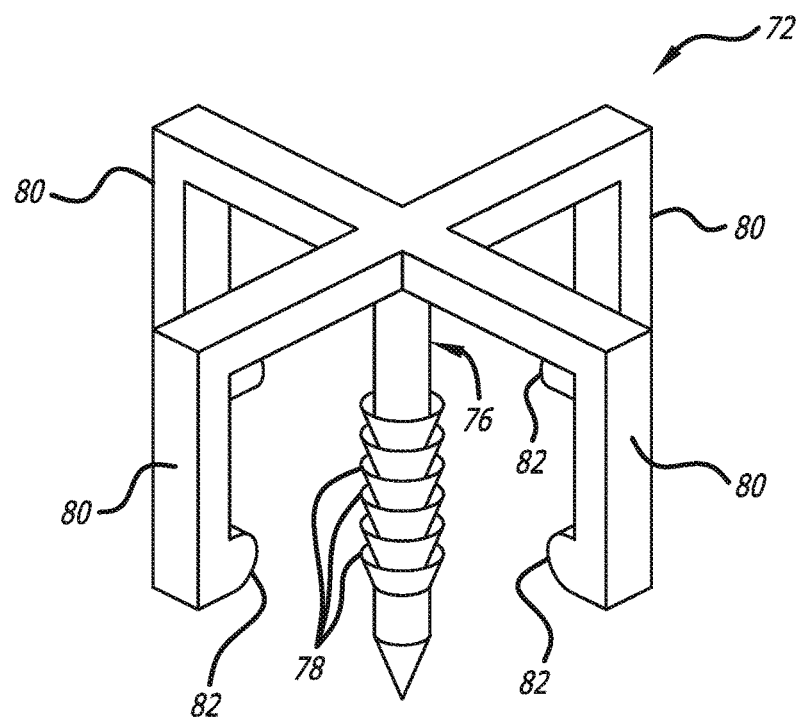
FIG. 11 is a perspective view of a component of the device of FIG. 10.

For example, FIG. 11 shows a spoked embodiment of the first component 72. Generally, the first component 72 includes a center spike 76 with one or more barbs 78. The first component 72 also includes one or more downward extensions 80 that include inward mating surfaces 82 configured to mate with the second component 74. These inward mating surfaces 82 ensure there is sufficient downward force on the radial extents of the first component 72 to induce necrosis.

The second component 74 is basically a cylindrical wall that includes an annular indentation 84 that accepts the inward mating surfaces 82 of the first component 72. The second component 74 further includes one or more disks 86 each defining a hole 88 through which the spike 76 is inserted when the components 72 and 74 are connected. The barbs 78 act against the disks 86 to lock the first component 72 to the second component 74.

Figure 12:
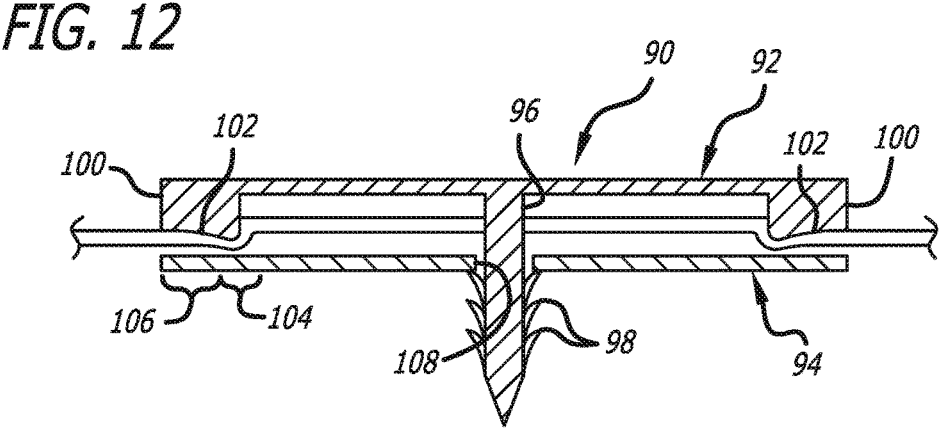
FIG. 12 is a cross-section of an embodiment of an anastomosis device of the present invention.
Figure 13:
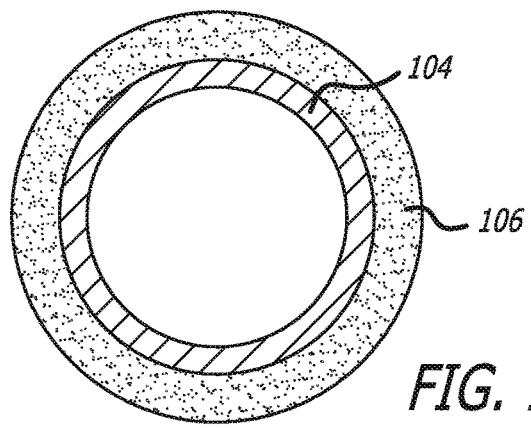
FIGS. 13 and 14 are depictions of anastomoses created by various embodiments of the device of FIG. 12.
Figure 14:
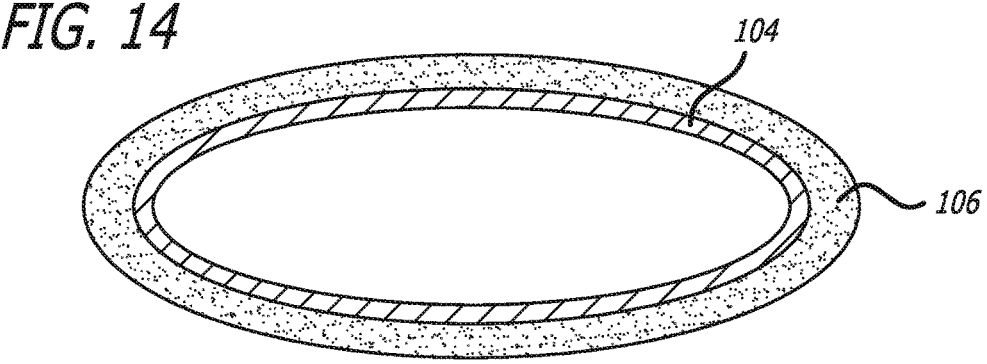

FIGS. 12-14 show another embodiment of an anastomosis device 90 of the present invention. The anastomosis device 90 includes a first component 92 and a second component 94. The first component 92 is a cap-like plate with a spike 96 extending downwardly therefrom and having a plurality of barbs 98. At its radial extents, the first component 92 includes a short peripheral wall 100 that terminates in a shaped surface 102. The shaped surface 102 is designed to create a necrosis zone 104 and a healing zone 106, due to the varying pressures exerted by the shaped surface 102 on tissue sandwiched between the first and second components 92 and 94.

The second component 94 is basically a disk that defines a center hole 108 for accepting the spike 96 and providing a surface against which the barbs 98 can act. The second component 94 is stiff enough to exert a squeezing force on tissue when connected to the first component 92. The device 90 may be a variety of shapes, including circular and oval. A circular embodiment is advantageous in that it allows automatic alignment of the two components 92 and 94 once the spike 96 is inserted into the center hole 108. However, a more elongate shape, such as an oval, may be more anatomically suited to the elongate configuration of the digestive tract.

FIGS. 13 and 14 show the resulting necrosis and healing zones 104 and 106 that result from circular and oval embodiments of the device 90. Because the inner necrosis zone 104 is continuous, only a thin band of tissue needs to necrose in order to create a comparatively large anastomosis.

Figure 17:
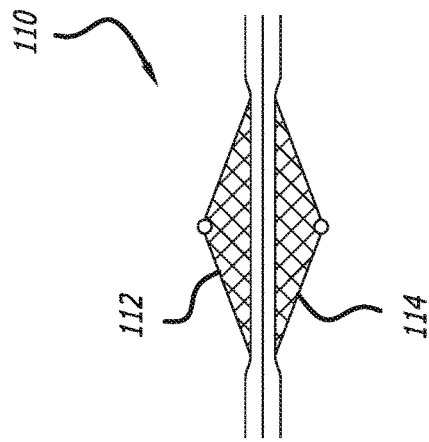
FIGS. 15-17 depict a deployment sequence of an embodiment of an anastomosis device of the present invention.
Figure 16:
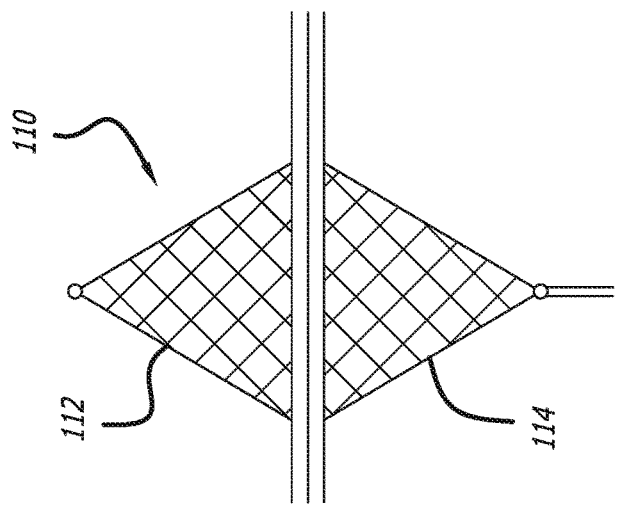
Figure 15:
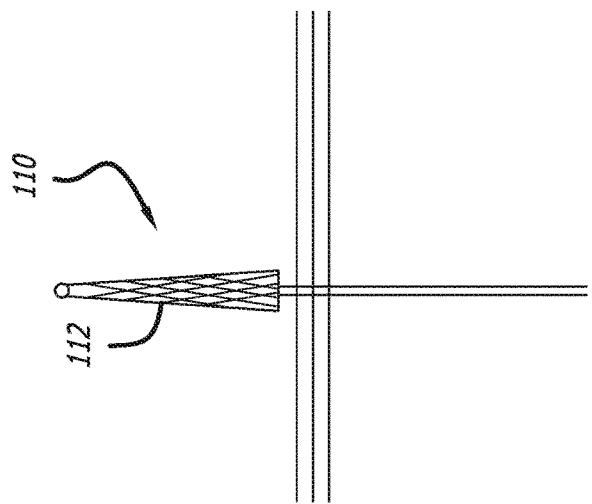

FIGS. 15-17 are sequential depictions of the deployment of an embodiment of an anastomosis device 110 of the present invention. The anastomosis device 110 includes a first component 112 and a second component 114. The first and second components 112 and 114 are both expandable mesh, umbrella-like devices that have collapsed and expanded configurations. It is envisioned that the first component 112 may collapsed to a point where it is possible to use the first component 112 to puncture through the duodenum and the ileum, possibly obviating the need to extend a guidewire 20 from the mouth to the rectum. FIG. 15 shows the first component 112 passing through two layers of tissue. FIG. 16 shows the first and second components 112 and 114 being expanded. FIG. 17 shows the fully expanded first and second components 112 and 114 being compressed against each other, thereby compressing the tissue therebetween to induce necrosis and create an anastomosis. The device 110 (and all of the devices described herein) may be constructed of any suitable material having sufficient strength to cause necrosis, such as stainless steel or Nitinol, for example. A fully expanded dome shape, such as that shown in FIG. 17 is preferable to ensure sufficient strength at the periphery of the device 110.

FIG. 18 shows another embodiment of an anastomosis device 120 of the present invention. The device 120 includes a first component 122 and a second component 124. The first component 122 is an elastomeric o-ring or band. The second component 124 is a continuous wall (such as a cylindrical wall, oval wall, elliptical wall or any desired shape) that includes an overhanging lip 126 around which the first component is stretched and secured, trapping tissue therebetween.

FIGS. 19-21 show a sequence of the first component 122 being of device 120 being attached to the second component. In FIG. 19, the second component 124 has been positioned against a layer of tissue, such as the inside wall of the ileum 16. FIG. 20 shows the second component 124 being pushed against the inside wall of the ileum 16 such that the ileum 16 comes in contact with another layer of tissue, such as that from the duodenum 12. FIG. 21 shows that the first component 122 has been stretched over the lip 126 of the second component 124, locking the tissue 12 and 16 around the device.

One advantage to using an anastomosis device with an elastomeric component providing squeezing force is that the force provided by an elastomeric component remains somewhat constant, even after necrosis begins to set in. In other words, if a mechanical device is used having first and second components that are a fixed distance from each other, the pressure placed on the tissue decreases as the tissue necroses and shrinks. An elastomeric component, on the other hand, will shrink with the tissue and continue to apply pressure.

Figure 22:
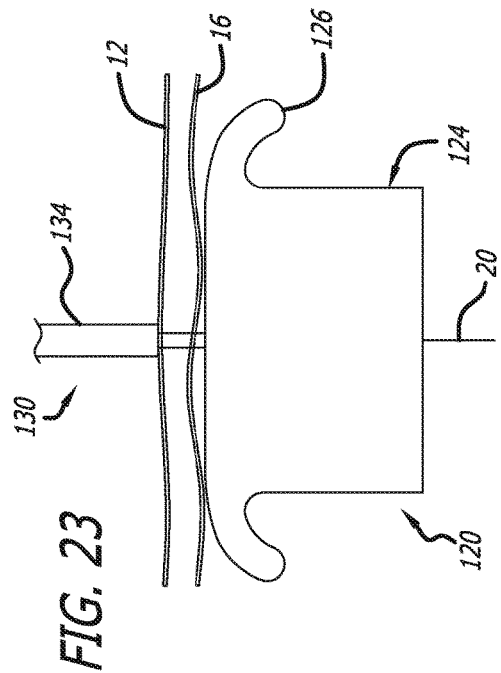
FIGS. 22-26 depict the use of a deployment device of the present invention being used to deploy an embodiment of the anastomosis device of the present invention.
Figure 23:
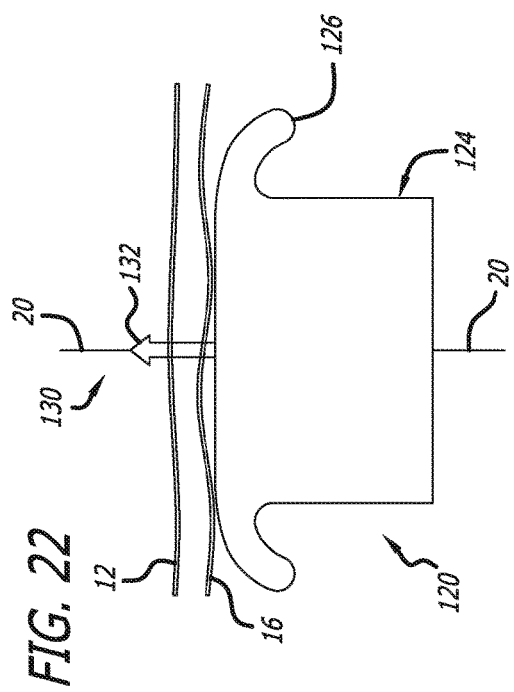

FIGS. 22-26 depict the use of a delivery device 130 of the present invention that may be used to connect the two components 122 and 124 of the anastomosis device 120. The delivery device 130 includes a centered spike 132 attached to the second component 124 and in the center thereof. The centered spike 132 is hollow and able to be advanced over the guidewire 20. The centered spike protrudes from the second component 124 such that when the second component 124 contacts tissue walls 12 and 16, the centered spike 132 pierces through the tissue and is available for connecting to a receiving tube 134 on the other side of the tissue walls 12 and 16. This is best shown in FIGS. 22 and 23.

Figure 24:
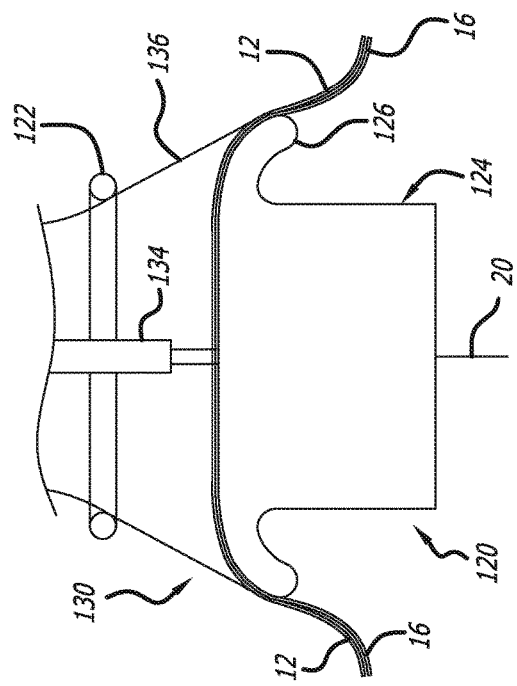

Referring to FIG. 24, it is shown that the delivery device 130 also includes a cone 136 that is able to slide over the receiving tube 134 and remain centered thereon. Because the centered spike 132 is concentric with the second component 124, and because the receiving tube 134 is concentric with both the centered spike 132 and the cone 136, the cone 136 may be advanced over the second component 124 without concern for alignment. Once the cone 136 is advanced over the second component, as shown, the elastomeric o-ring 122 may be stretched over the cone. This may be accomplished, for example, via a pusher sheath.

Figure 25:
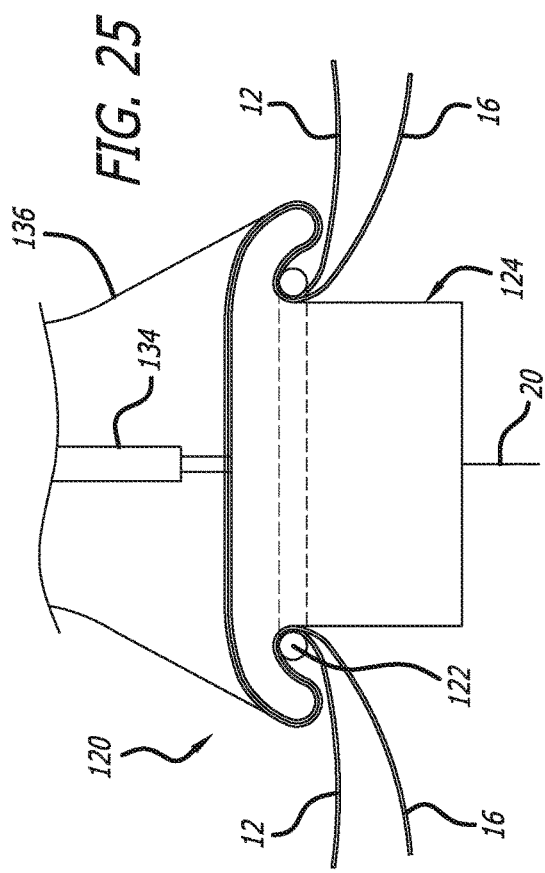
Figure 26:
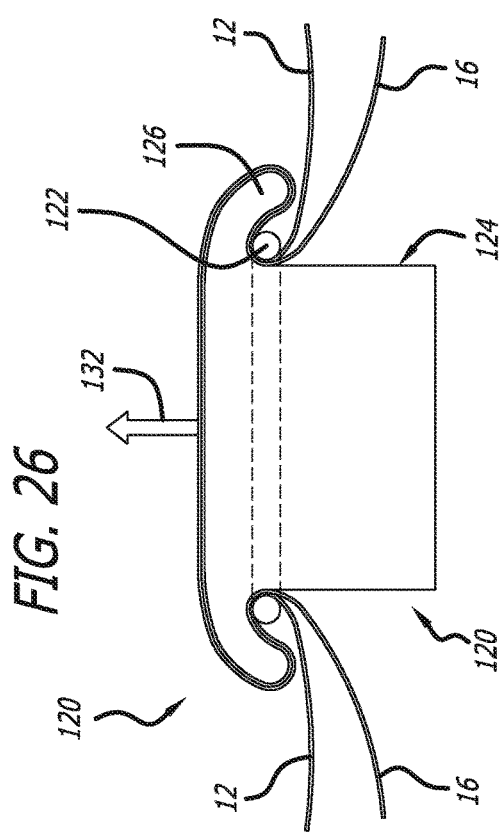

FIG. 25 shows that the o-ring 122 has been advanced over the cone 136 and is in place under the lip 126 of the second component 124. FIG. 26 shows the device 120 in place after the delivery device 130 and the guidewire 20 have been removed.

Figure 27:
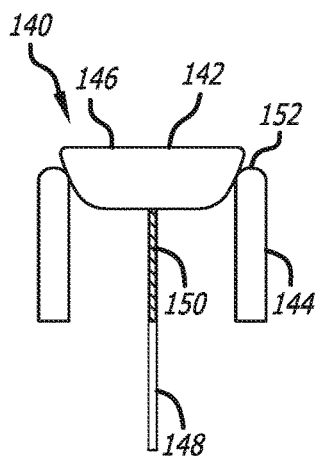
FIGS. 27-29 depict a deployment sequence of an embodiment of an anastomosis device of the present invention.
Figure 28:
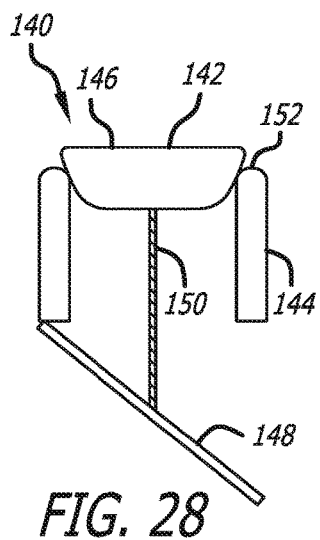
Figure 29:
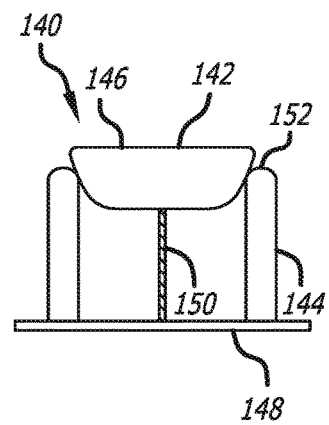
Figure 30:
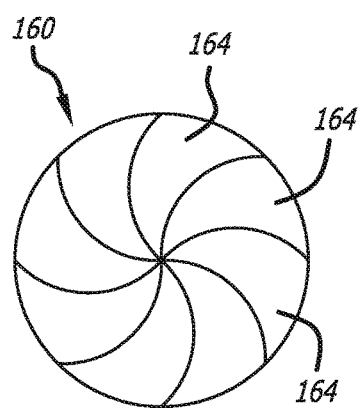
FIGS. 30-33 depict expanded and collapsed configurations of an embodiment of an anastomosis device of the present invention.
Figure 32:
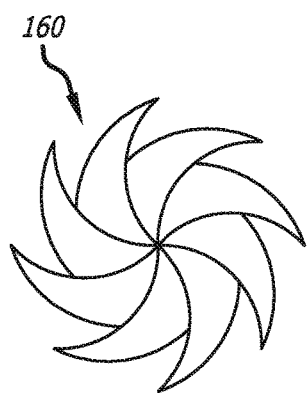

FIGS. 27-29 show an embodiment of an anastomosis device 140. The device 140 includes a first component 142 and a second component 144. The first component 142 includes a cup 146 connected to an anchor bar 148 with an elastic connector 150. The elastic connector 150 may be an elastomeric band or a spring.

The second component 144 is a cylinder, preferably with a rounded edge 152 that makes contact with tissue. In operation, as seen in the sequence shown in FIGS. 27-29, the first component 142 is advanced through a first digestive passage, such as the duodenum, while the second component 144 is advanced through a second digestive passage, such as the ileum. The anchor bar 148 is aligned with the connector 150 and both are passed through a small hole to the ileum and through the second component 144. The connector 150 is stretched sufficiently to allow the anchor bar 148 to pass completely through the second component and rotate to hold the second component 144 against the cup 146 of the first component 142. Because the connector 150 is stretched, constant pressure is applied to the tissue trapped between the cup 146 and the first component 142.

Figure 31:
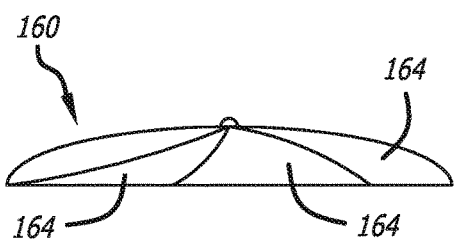
Figure 33:
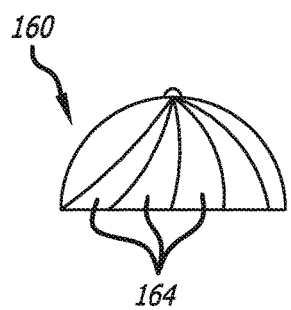

FIGS. 30-33 show deployed and collapsed configurations of an embodiment of an anastomosis device 160 of the present invention. The device 160 includes a first component 162 and a second component, which is the essentially the same as the first component 162. The device 160 is similar to the device 110 of FIGS. 15-17 except in that a solid material is used instead of a mesh, thereby adding strength to the device. The component 162 is made up of a plurality of shaped plates 164 that slide against each other in order to transition from collapsed to deployed configurations. FIG. 31 illustrates that in the deployed configuration, the device 160 is domed, thereby providing pressure against the tissue at the periphery of the device 160.

Figure 34:
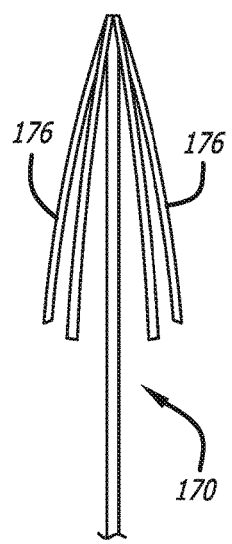
FIG. 34 is a perspective view of a collapsed configuration of an embodiment of an anastomosis device of the present invention.
Figure 35:
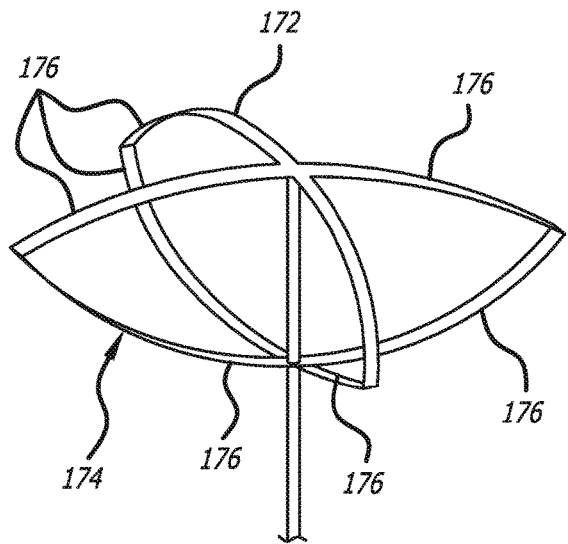
FIG. 35 is a perspective view of an expanded configuration of the embodiment of an anastomosis device of FIG. 34.
Figure 36:
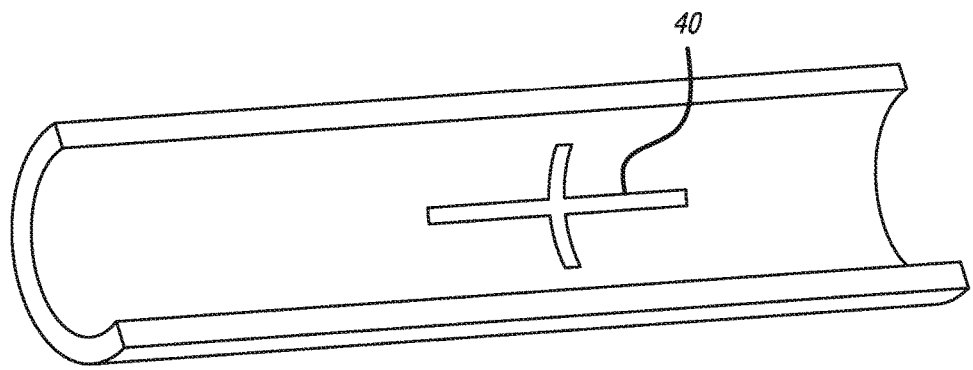
FIG. 36 is a perspective view of the anastomosis formed by the device of FIGS. 34 and 35.

FIGS. 34-36 show deployed and collapsed configurations of an embodiment of an anastomosis device 170 of the present invention. The device 170 includes a first component 172 and a second component 174, which is the essentially the same as the first component 172. The device 170 demonstrates that shapes other than circular may be used to create anastomosis. The first and second components 172 and 174 of device 170 each include a plurality of corresponding arms 176. Preferably, as shown in FIG. 35, in the deployed configuration, the device 170 is domed, thereby providing pressure against the tissue at the distal ends of the arms 176. FIG. 36 shows the resulting anastomosis 40 created by the device 170. It is noted that the proximal side of the device 170, that is the side of the device that is not passing through tissue, would not have to be expandable.

Figure 37:
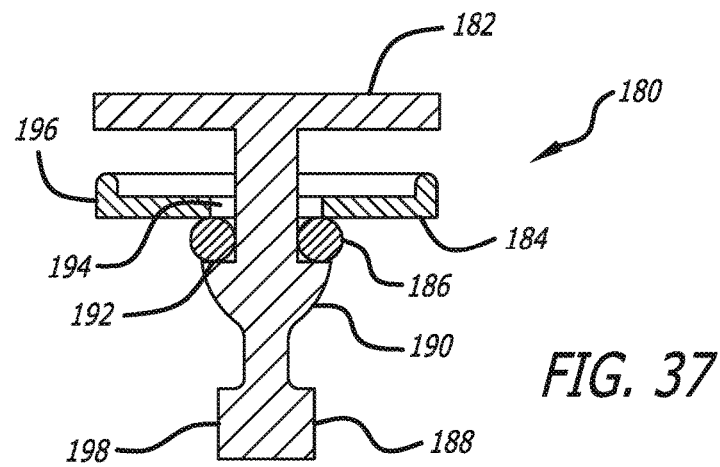
FIG. 37 is a cross-sectional view of an embodiment of an anastomosis device of the present invention.

FIG. 37 shows an embodiment of an anastomosis device 180 of the present invention. The device 180 generally includes a first component 182, a second component 184, and an elastic o-ring 186. The first component 182 has a center pin 188 extending downwardly therefrom and is shaped to include a ramp 190 and a ledge 192, which are used to stretch and contain the o-ring 186. The center pin 188 also may include a distal bulb 198 for use in conjunction with a delivery device such as the device 200 shown in FIG. 38.

The second component 184 is a disk defining a center hole 194 for accepting the pin 188 and may include an annular pressure ridge 196 for exerting pressure on the compressed tissue between the two components 182 and 184. The elastomeric o-ring 186 functions to lock the two components 182 and 184 together and also to exert steady force on the second component 184.

Figure 38:
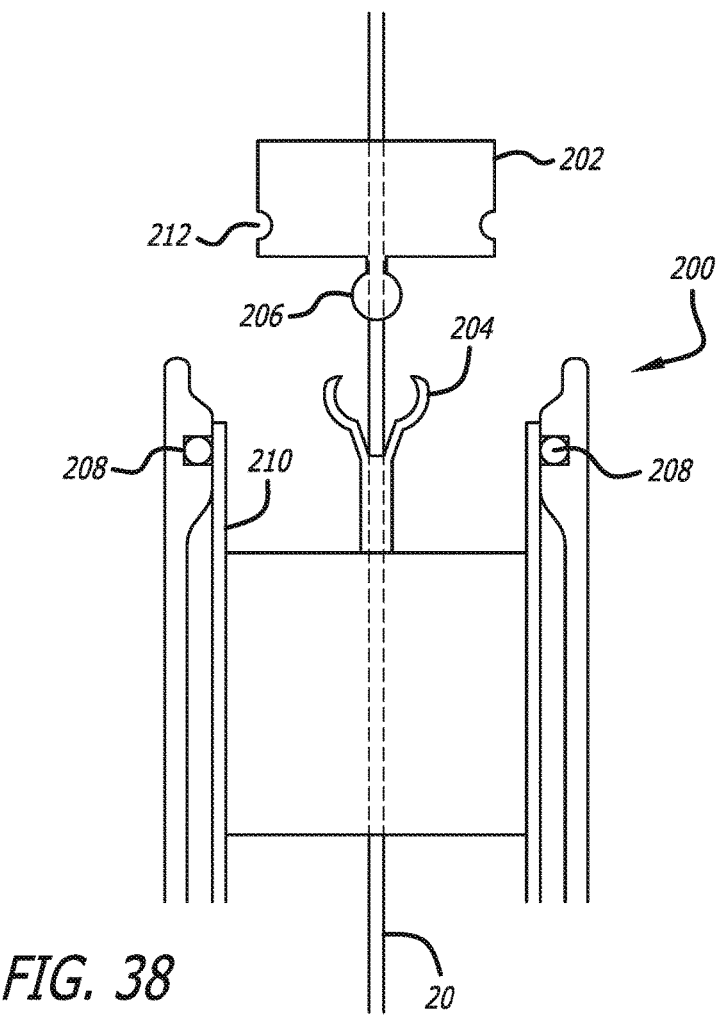
FIG. 38 is a cross-sectional view of an embodiment of a delivery device of the present invention.

FIG. 38 depicts an embodiment of a delivery device 200 of the present invention that may be used to connect two components of a delivery device together, wherein the second component is an o-ring. The delivery device 200 works in conjunction with a guidewire 20, which passes through the delivery device and through a first component 202 of an anastomosis device. The device 200 generally includes a grabbing device 204, which is used to grab a bulb 206 of the first component 202. The grabbing device 204 can then be used to pull the first component into the delivery device 200, which contains the second component, o-ring 208. It is understood that by pulling the first component 202 into the device 200, tissue is being trapped between the two components 202 and 208.

The o-ring 208 is being held in an expanded state by an inner sheath 210. Once the first component 202 is in place such that a receiving indentation 212 is aligned with the o-ring 208, the sheath 210 is retracted, thereby releasing the o-ring.

Figure 39:
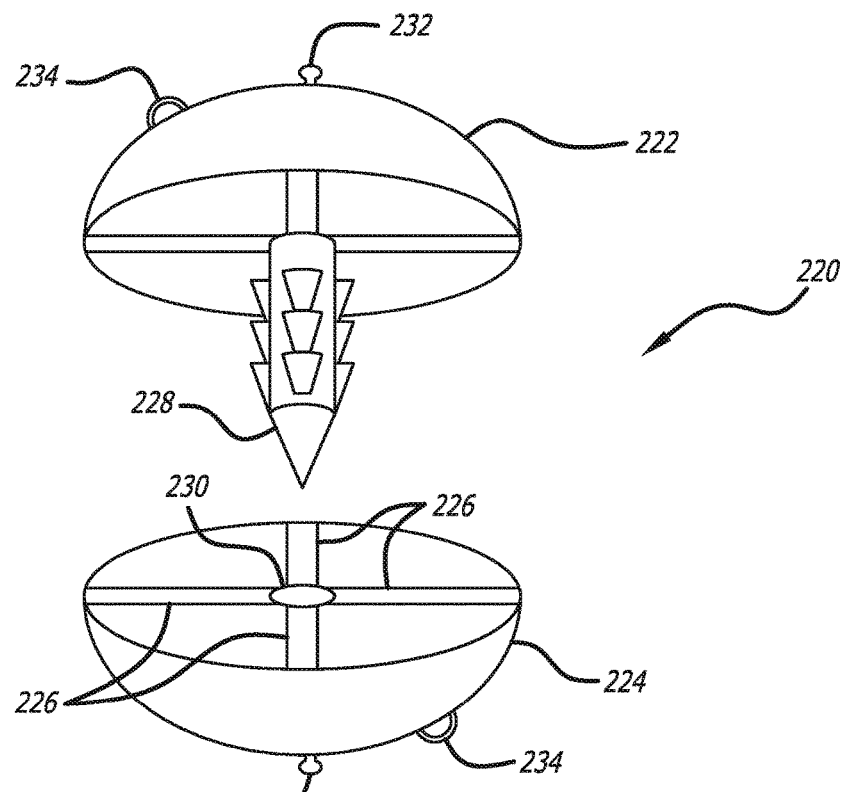
FIG. 39 is a perspective view of an embodiment of an anastomosis device of the present invention.
Figure 40:
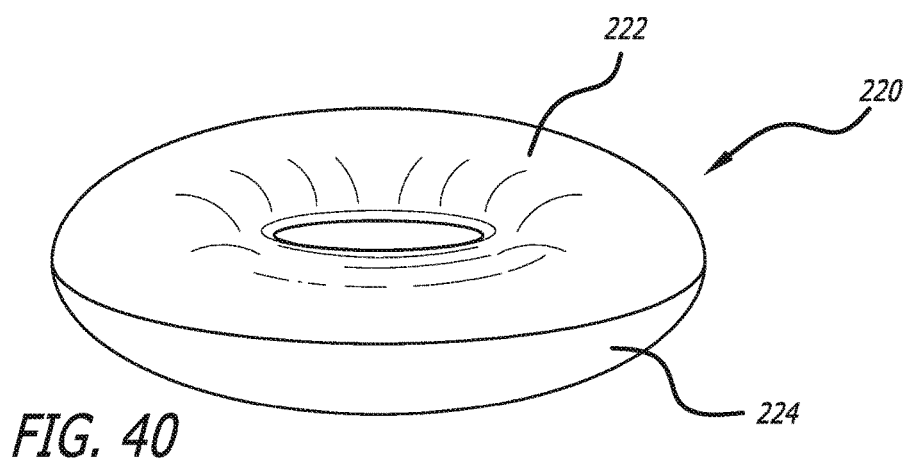
FIG. 40 is a perspective view of an embodiment of an anastomosis device of the present invention.

FIGS. 39 and 40 show an embodiment of an anastomosis device 220 of the present invention. The device 220 includes a first component 222 and a second component 224. Both components 222 and 224 have a domed, clam-shell like design supported by braces 226. The first component 222 also includes a barbed spike 228. The barbed spike 228 preferably extends from an inside surface of the clam shell and slides through an opening supported by the braces 226. The spike 228 is configured to pass through a similar opening 230 supported by the braces 226 of the second component 224. The two components 222 and 224 can thus be compressed together, as shown in FIG. 40. Each component 222 and 224 could be compressible or made of a material such as Nitinol that expands after reaching the implant site. In order to more easily deliver the components 222 and 224, the components may be equipped with attachment points 232 for a guide wire, and may also contain loops 234, through which the guide wire or auxiliary mandrel passes in order to maintain the components 222 and 224 in a sideways configuration while navigating through the digestive tract to the target site. The loops 234 are released upon reaching the target site, thereby allowing the components 222 and 224 to face each other. Though the curved "shell" portions of each component 222 and 224 are shown as being solid, the device 220 would function with a mesh or skeletal shell as well.

Figure 41:
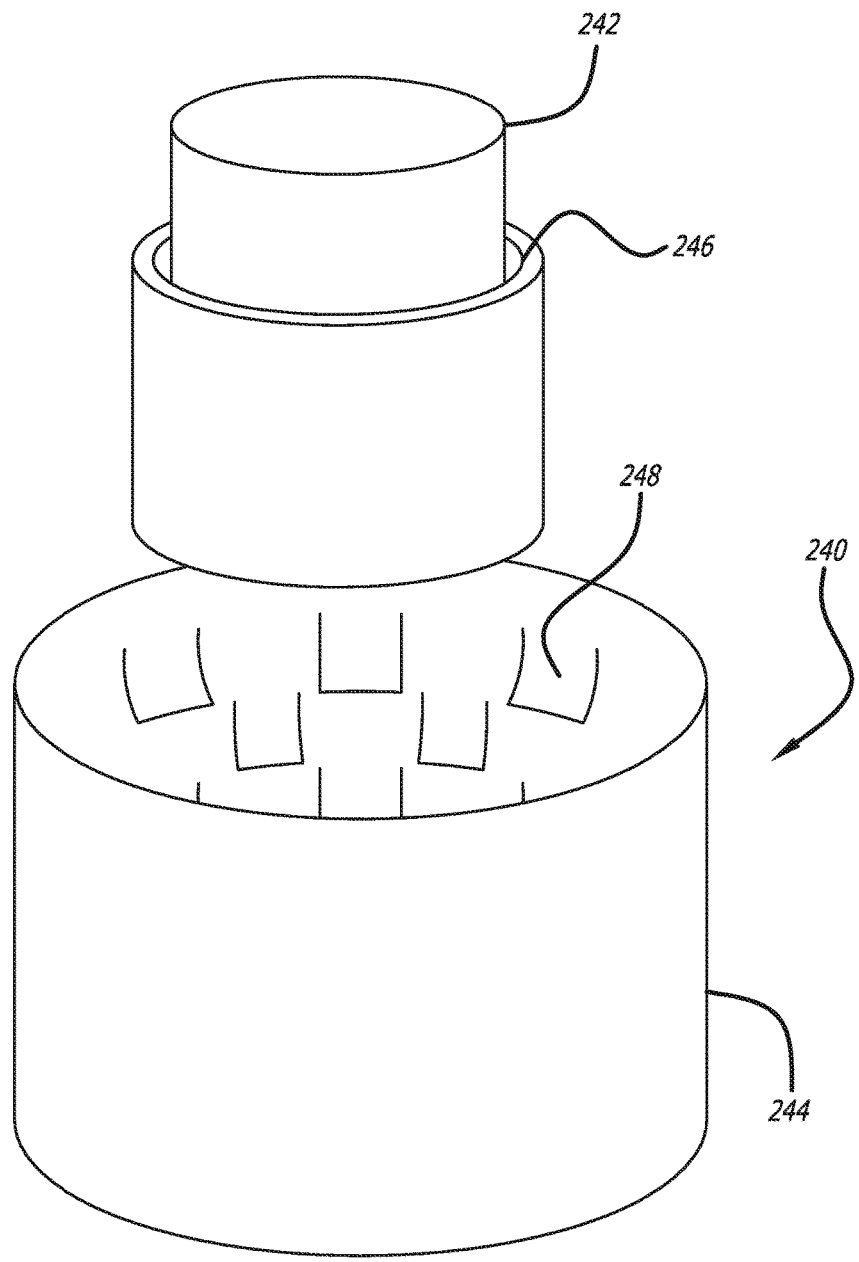
FIG. 41 is a perspective view of an embodiment of an anastomosis device of the present invention; and, FIG. 42 is a diagram showing various anastomosis sites.

FIGS. 10-12 and 39 show embodiments of devices held together with barbed spikes. FIG. 41 shows an alternative attachment mechanism 240. This mechanism 240 includes a male component 242 and a female component 244. The male component 242 is a plug that has an circumferential lip 246. The female component 244 includes a plurality of inward-projecting tabs 248. As the male component 242 is inserted into the female component 244, the tabs 248 expand over the lip 246 such that the male component 242 cannot be retracted from the female component 244.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

We claim:

1. A method for creating an anastomosis between two locations in a body lumen comprising:
   placing a first element in a first location of a body lumen by using a first delivery device to navigate to said first location via a natural orifice;
   placing an elastic second element in a second location of said body lumen by using a second delivery device to navigate to said second location via a natural orifice;
   stretching said elastic second element over said first element, thereby trapping tissue from said first and second locations between said first and second elements, while the elastic second element is maintained in an elastic state;
   leaving said first and second elements in the body lumen while allowing material to flow naturally around the first and second elements while the first and second elements are creating a side-to-side pressure anastomosis between the first and second locations;
   wherein no living tissue is cut or excised before or after the second element is placed over the first element; and,
   wherein once said anastomosis is formed, some material flows naturally through the lumen and some material flows through the anastomosis.

2. The method according to claim 1 wherein placing a first element in a first location comprises placing a first element having a continuous wall and an overhanging lip radiating therefrom in a first location.

3. The method of claim 2 wherein stretching said elastic second element over said first element comprises stretching said elastic second element over said overhanging lip.

4. The method of claim 3 wherein stretching said elastic second element over said overhanging lip comprises advancing said elastic second element over a conical portion of a delivery device placed proximate said overhanging lip.

5. The method of claim 1 wherein placing an elastic second element in a second location comprises placing an elastic o-ring in said second location.

6. The method of claim 1, wherein:
the elastic second element comprises an O-ring; and
the first element comprises:
  a tubular portion having a cylindrical side wall with a proximal end and a distal end;
  an overhanging lip radiating from the distal end of the cylindrical side wall and extending back toward the proximal end, the overhanging lip tapering outward toward the proximal end, terminating in an annular tip and defining a recess between the overhanging lip and an opposed portion of the cylindrical wall;
wherein the stretching of the elastic second element over the first element comprises stretching the O-ring over the overhanging lip and over the annular tip thereof, and wherein the O-ring elastically moved from the annular tip into the recess, thereby trapping the tissue within the recess.

7. The method of claim 6, wherein the stretching of the elastic second element over the first element comprises placing a conical element proximate to the distal end of the tubular portion of the first element and advancing the O-ring over the conical element.

8. The method of claim 7, wherein the conical element is placed against part of the overhanging lip proximate to the annular tip, the O-ring is advanced and stretched during advancement over the conical element, and the O-ring is then advanced off of the conical element and over the annular tip.

9. A method for creating an anastomosis between two locations in a body lumen comprising:
placing a first element in a first location against a first wall of a body lumen by using a first delivery device to navigate to said first location via a natural orifice;
placing an elastic second element in a second location against a second wall of said body lumen, wherein said first wall and said second wall of tissue are adjacent, and wherein said first and second elements are opposed and separated by said first and second walls by using a second delivery device to navigate to said second location via a natural orifice;
placing the elastic second element over said first element, thereby trapping first and second walls between said first and second elements;
stretching said elastic second element thereby creating a side-to-side pressure anastomosis between the first and second locations;
wherein the step of placing the elastic second element over said first element causes said stretching of said elastic second element and the elastic second element is maintained in an elastic state throughout the placing step;
wherein material naturally flowing through said lumen is allowed to continue to flow through said lumen during a period of time between when said first and second elements are placed and when said anastomosis is formed;
wherein no living tissue is cut or excised before or after the second element is placed over the first element; and,
wherein once said anastomosis is formed, some material flows naturally through the lumen and some material flows through the anastomosis.

10. The method of claim 9 further comprising allowing said first element, said elastic second element, and necrosed tissue to pass through one of said first and second locations after said pressure anastomosis has formed.

\* \* \* \* \*